(12) United States Patent
Yerxa et al.

(10) Patent No.: US 7,091,334 B2
(45) Date of Patent: *Aug. 15, 2006

(54) METHOD FOR LARGE-SCALE PRODUCTION OF DI(URIDINE 5')-TETRAPHOSPHATE AND SALTS THEREOF

(75) Inventors: Benjamin R. Yerxa, Raleigh, NC (US); William Pendergast, Durham, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 16 days.

This patent is subject to a terminal disclaimer.

(21) Appl. No.: 10/895,728

(22) Filed: Jul. 20, 2004

(65) Prior Publication Data

US 2004/0267005 A1    Dec. 30, 2004

Related U.S. Application Data

(63) Continuation of application No. 09/805,332, filed on Mar. 12, 2001, now Pat. No. 6,765,090, which is a continuation of application No. 09/122,516, filed on Jul. 24, 1998, now Pat. No. 6,319,908.

(60) Provisional application No. 60/054,147, filed on Jul. 25, 1997.

(51) Int. Cl.
C07H 21/02    (2006.01)

(52) U.S. Cl. ............... 536/26.22; 536/55.3; 536/26.2

(58) Field of Classification Search ............ 536/26.2, 536/55.3, 26.22
See application file for complete search history.

(56) References Cited

U.S. PATENT DOCUMENTS

| | | | |
|---|---|---|---|
| 4,136,175 A | 1/1979 | Rideout et al. | 514/47 |
| 5,032,680 A | 7/1991 | Kawai et al. | 514/50 |
| 5,292,498 A | 3/1994 | Boucher | 424/45 |
| 5,449,664 A | 9/1995 | Verheyden et al. | 514/45 |
| 5,596,088 A | 1/1997 | Boucher et al. | 536/23.5 |
| 5,607,836 A | 3/1997 | Boucher et al. | 435/7.2 |
| 5,628,984 A | 5/1997 | Boucher | 424/45 |
| 5,635,160 A | 6/1997 | Stutts, III et al. | 424/45 |
| 5,656,256 A | 8/1997 | Boucher et al. | 435/7 |
| 5,691,156 A | 11/1997 | Boucher et al. | 435/7.21 |
| 5,763,447 A | 6/1998 | Jacobus et al. | 514/265 |
| 5,789,391 A | 8/1998 | Jacobus et al. | 424/45 |
| 5,837,861 A | 11/1998 | Pendergast et al. | 536/25.6 |
| 5,900,407 A | 5/1999 | Yerxa et al. | 514/47 |
| 5,902,567 A | 5/1999 | Boucher | 424/9.1 |
| 5,935,555 A | 8/1999 | Stutts et al. | 424/45 |
| 5,958,897 A | 9/1999 | Jacobus et al. | 514/49 |
| 5,962,432 A | 10/1999 | LaCroix et al. | 514/47 |
| 5,968,913 A | 10/1999 | LaCroix et al. | 514/47 |
| 5,972,904 A | 10/1999 | Jacobus et al. | 514/51 |
| 5,981,506 A | 11/1999 | Jacobus et al. | 514/47 |
| 6,022,527 A | 2/2000 | Boucher et al. | 424/45 |
| 6,133,247 A | 10/2000 | Boucher | 514/50 |
| 6,143,279 A | 11/2000 | Boucher et al. | 424/45 |
| 6,159,952 A | 12/2000 | Shaffer et al. | 514/47 |
| 6,765,090 B1 * | 7/2004 | Yerxa et al. | 536/26.2 |

FOREIGN PATENT DOCUMENTS

| | | |
|---|---|---|
| WO | WO 96/40059 | 12/1996 |
| WO | WO 97/29456 | 8/1997 |
| WO | WO 97/29756 | 8/1997 |
| WO | WO 97/35591 | 10/1997 |
| WO | WO 98/03177 | 1/1998 |
| WO | WO 98/03182 | 1/1998 |
| WO | WO 98/15835 | 4/1998 |
| WO | WO 98/19685 | 5/1998 |
| WO | WO 98/34593 | 8/1998 |
| WO | WO 98/34942 | 8/1998 |

(Continued)

OTHER PUBLICATIONS

Coste et al., "Non-adenylylated Bis(5'-nucleosidyl) Tetraphosphates Occur in *Saccharomyces cerevisiae* and in *Escherichia coli* and Accumulate upon Temperature Shift or Exposure to Cadmium," *J. Biol. Chem.* 262(25): 12096-12103 (1987).

(Continued)

*Primary Examiner*—S. Anna Jiang
*Assistant Examiner*—L. E. Crane
(74) *Attorney, Agent, or Firm*—Howrey LLP; Viola T. Kung

(57) ABSTRACT

The present invention provides new methods for the synthesis of the therapeutic dinucleotide, $P^1,P^4$-di(uridine 5')-tetraphosphate, and demonstrates applicability to the production of large quantities. The methods of the present invention substantially reduce the time period required to synthesize diuridine tetraphosphate, preferably to three days or less. The novel tetrammonium and tetrasodium salts of $P^1,P^4$-di(uridine 5')-tetraphosphate (Formula I) prepared by these methods are stable, soluble, nontoxic, and easy to handle during manufacture.

Formula I

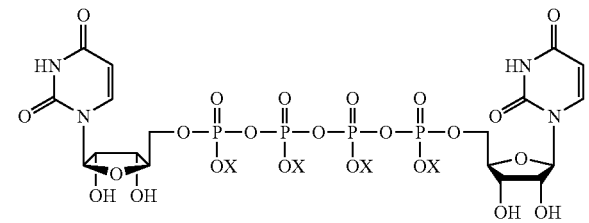

wherein:
X is Na, $NH_4$ or H, provided that all X groups are not H.

18 Claims, No Drawings

FOREIGN PATENT DOCUMENTS

| | | |
|---|---|---|
| WO | WO 99/01138 | 1/1999 |
| WO | WO 99/05155 | 2/1999 |
| WO | WO 99/09998 | 3/1999 |
| WO | WO 99/32085 | 3/1999 |
| WO | WO 99/61012 | 12/1999 |
| WO | WO 00/30629 | 6/2000 |
| WO | WO 00/39145 | 7/2000 |
| WO | WO 00/50024 | 8/2000 |

OTHER PUBLICATIONS

Guranowski et al., "Synthesis of Diadenosine 5',5'-$P^1$,$P^4$-Tetraphosphate (AppppA) from Adenosine 5'-Phosphosulfate and Adenosine 5'-Triphosphate Catalyzed by Yeast AppppA Phosphorylase," *Biochemistry* 27: 2959-2964 (1988).

Lobaton et al., "Diguanosinetetraphosphatase from Rat Liver: Activity on Diadenosine Tetraphosphate and Inhibition by Adenosine Tetraphosphate," *Eur. J. Biochem.* 50: 494-501 (1975).

Ng. E. and Orgel, L., "The action of a water-soluable carbodiimide and adenosine-5'-polyphosphates," *Nucleic Acid Res.* 15(8): 3573-3580 (1987).

Olivier, K., et al., "Acute Safety and Effects on Mucociliary Clearance of Aerosolized Uridine 5'-Triphosphate + Amiloride in Normal Human Adults," *Am. J. Respir. Crit. Care Med.* 154: 217-223 (1996).

Rapaport et al., "HeLa cell DNA polymerase α is tightly associated with tryptophanyl-tRNA synthetase and diadenosine 5',5'-$P^1$,$P^4$-tetraphosphate binding activities," *Proc. Natl. Acad. Sci.* 78(2): 838-842 (1981).

Sillero et al., "Dinucleosidetriphosphatase from Rat Liver," *Eur.J. Biochem.* 76: 331-337 (1977).

Vallejo et al., "Dinucleosidasetetraphosphatase in Rat Liver and *Artemia salina*," *Biochem. Biophy. Acta* 438: 304-309 (1976).

\* cited by examiner

METHOD FOR LARGE-SCALE PRODUCTION OF DI(URIDINE 5')-TETRAPHOSPHATE AND SALTS THEREOF

This application is a continuation of U.S. application Ser. No. 09/805,332, filed Mar. 12, 2001, now U.S. Pat. No. 6,765,090, which is a continuation of U.S. application Ser. No. 09/122,516, filed Jul. 24, 1998, now U.S. Pat. No. 6,319,908; which claims priority to U.S. Provisional Application No. 60/054,147 filed Jul. 25, 1997. The above applications are incorporated herein by reference in their entirety.

TECHNICAL FIELD

This invention relates to methods for the production of therapeutic dinucleotides including novel salts thereof. More specifically, it relates to methods for synthesis of $P^1,P^4$-di(uridine 5')-tetraphosphate, i.e., diuridine tetraphosphate ($U_2P_4$) which have advantages over prior art methods of manufacture.

BACKGROUND OF THE INVENTION $P^1,P^4$-Di(uridine 5')-tetraphosphate is a dinucleotide of the following structure:

Formula I

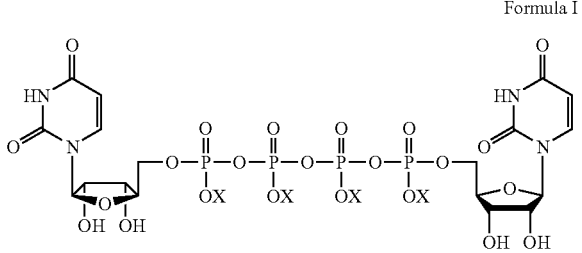

wherein:

X is Na, $NH_4$ or H, provided that all X groups are not H.

The free acid of $P^1,P^4$-di(uridine 5')-tetraphosphate, where X is hydrogen, has been previously described as uridine 5'-(pentahydrogen tetraphosphate), $P'''\rightarrow 5'$-ester with uridine (CAS Registry Number: 59985-21-6; C. Vallejo et al., *Biochimica et Biophysica Acta* 438, 305 (1976) and H. Coste et al., *J. Biol. Chem.* 262, 12096 (1987)).

Different methods have been described for the synthesis of purine dinucleotides such as diadenosine tetraphosphate ($A_2P_4$) (E. Rappaport et al, *Proc. Natl. Acad. Sci*, 78, 838, (1981); A. Guranowski et al, *Biochemistry*, 27, 2959, (1988); C. Lobaton et al, *Eur. J. Biochem.*, 50, 495, 1975; K. Ng and L. Orgel, *Nucl. Acid Res.*, 15, 3573, (1987)). However, this has not been true for $U_2P_4$ which is a pyrimidine nucleotide. Although purine nucleotides and pyrimidine nucleotides appear to be analogous, the methods used for purine nucleotide synthesis do not necessarily work for pyrimidines such as uridine.

Diuridine tetraphosphate has been shown to have beneficial properties in the treatment of various diseases, such as chronic obstructive pulmonary disease (COPD). For example, they have been demonstrated to facilitate the clearance of mucous secretions from the lungs of a subject such as a mammal including humans in need of treatment for various reasons, including cystic fibrosis, chronic bronchitis, asthma, bronchiectasis, post-operative mucous retention, pneumonia, primary ciliary dyskinesia (M. J. Stutts, III, et al, U.S. Pat. No. 5,635,160; PCT International Publication WO 96/40059) and the prevention and treatment of pneumonia in immobilized patients (K. M. Jacobus and H. J. Leighton, U.S. Pat. No. 5,763,447). Further therapeutic uses include treatment of sinusitis (PCT International Publication WO 98/03177), otitis media (PCT International Publication WO 97/29756), dry eye, retinal detachment, nasolacrimal duct obstruction, the treatment of female infertility and irritation due to vaginal dryness via increased mucus secretions and hydration of the epithelial surface, and enhancing the performance of athletes.

$U_2P_4$ also has utility as a veterinary product in mammals such as, but not limited to, dogs, cats and horses.

Prior art methodology describes only one protocol for the production of diuridine tetraphosphate. This method is very time consuming, lasting over five days and producing only small amounts of diuridine tetraphosphate (C. Vallejo et al., *Biochimica et Biophysica Acta* 438, 305 (1976), Sillero et al., *Eur J Biochem* 76, 332 (1972)). According to this technique, diuridine tetraphosphate was synthesized through a reaction of uridine 5'-monophosphomorpholidate (0.54 mmol) with the triethylamine salt of pyrophosphoric acid (0.35 mmol) in a medium of anhydrous pyridine (10 ml). After 5 days at 30° C., pyridine was removed from the reaction mixture by evaporation, and the residue resuspended in glass-distilled water (8 mL), the suspension applied to a DEAE-cellulose column (37.5×2.6 cm) and fractionated with 3.2 L of a linear gradient (0.06–0.25 M) of ammonium bicarbonate, pH 8.6. The peak eluting between 0.17–0.19 M ammonium bicarbonate was partially characterized as $U_2P_4$ by the following criteria: insensitivity to alkaline phosphatase, phosphorus to base ratio and analysis of the products of hydrolysis (UTP+UMP), after treatment with phosphodiesterase I, by electrophoresis in citrate buffer, pH 5.0. No yield or spectroscopic data were given. Thus, the prior art procedure for the synthesis of diuridine tetraphosphate is lengthy and produced only small amounts of only partially characterized diuridine tetraphosphate. The present invention focuses on methods to produce this medically useful compound which may be more efficiently and conveniently carried out, and which may be applied to the large-scale production of diuridine tetraphosphate and salts thereof.

SUMMARY OF THE INVENTION

The present invention provides new methods for the synthesis of the therapeutic dinucleotide, $P^1,P^4$-di(uridine 5')-tetraphosphate (Formula I), and demonstrates applicability to the production of large quantities. The methods of the present invention substantially reduce the time required to synthesize diuridine tetraphosphate, preferably to three days or less. The novel ammonium and sodium salts of $P^1,P^4$-di(uridine 5')-tetraphosphate prepared by these methods are stable, soluble, nontoxic, and easy to handle during manufacture. The tetraammonium salt is preferred; the tetrasodium salt is most preferred.

Formula I

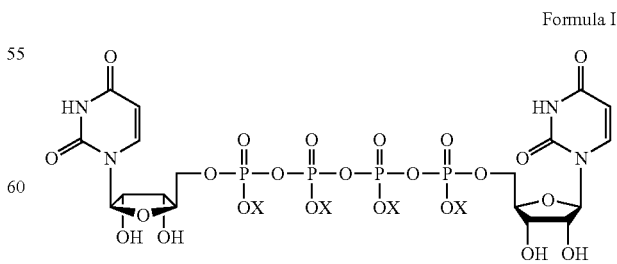

wherein:

X is $Na^+$, $NH_4^+$ or H, provided that all X groups are not H.

The method of synthesizing compounds of Formula I, and pharmaceutically acceptable salts thereof, is carried out generally by the following steps: 1) dissolving uridine or uridine nucleotide compounds of Formulas IIa–d in a polar, aprotic organic solvent and a hydrophobic amine; 2) phosphorylating with a phosphorylating agent of Formulas IVa–b and/or activating with an activating agent of Formulas IIIa–c; and 3) purifying by ion exchange chromatography.

Another aspect of the present invention are methods of treating various disease states, including, but not limited to: chronic obstructive pulmonary diseases, sinusitis, otitis media, nasolacrimal duct obstruction, dry eye disease, retinal detachment, pneumonia, and female infertility or irritation caused by vaginal dryness.

Another aspect of the present invention is a pharmaceutical composition comprising a compound of Formula I together with a pharmaceutically acceptable carrier.

DETAILED DESCRIPTION OF THE INVENTION

The present invention provides new methods for the synthesis of the therapeutic dinucleotide, $P^1,P^4$-di(uridine 5')-tetraphosphate, and demonstrates applicability to the production of large quantities. The methods of the present invention substantially reduce the time period required to synthesize $P^1,P^4$-di(uridine 5')-tetraphosphate, preferably to three days or less. The ammonium and sodium salts of $P^1,P^4$-di(uridine 5')-tetraphosphate (Formula I) prepared by these methods are stable, soluble, nontoxic, and easy to handle during manufacture.

The present invention further provides compounds of Formula I:

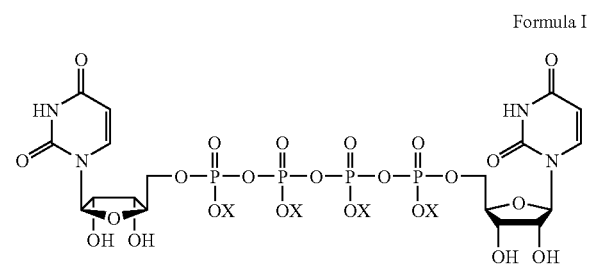

Formula I wherein:

X is $Na^+$, $NH_4^+$ or H, provided that all X groups are not H.

The sodium and ammonium salts of $P^1,P^4$-di(uridine 5')-tetraphosphate have many advantages. The sodium and ammonium salts provide good long-term stability profiles compared to those of divalent cations (e.g. $Ca^{2+}$, $Mg^{2+}$, $Mn^{2+}$) which catalyze hydrolysis of phosphate esters. The tetrasodium salt of $P^1,P^4$-di(uridine 5')-tetraphosphate is non-irritating to the lung and eyes. Other cations may be irritating to the lungs, eyes, and other mucosal epithelia, or are otherwise not well tolerated by the human body. These inorganic sodium and ammonium salts impart excellent water solubility compared to hydrophobic amine salts such as tri- and tetrabutylammonium, and similar salts. High water solubility is an important advantage for flexibility in pharmaceutical formulations of varying concentration. The tetrammonium and tetrasodium salts of $P^1,P^4$-di(uridine 5')-tetraphosphate are also advantageous in that they are readily purified by aqueous ion chromatography in which no organic solvents are used. In addition, these salts are easily handled as fluffy, white solids, compared to an oil or gum as with some amine salts.

The tetrasodium salt is preferred.

The compounds of Formula I may be used to facilitate the clearance of mucous secretions from the lungs of a subject such as a mammal including humans in need of treatment for various reasons, including cystic fibrosis, chronic bronchitis, asthma, bronchiectasis, post-operative mucous retention, pneumonia, primary ciliary dyskinesia (M. J. Stutts, III, et al, U.S. Pat. No. 5,635,160; PCT International Publication WO 96/40059) and the prevention and treatment of pneumonia in immobilized patients (K. M. Jacobus and H. J. Leighton, U.S. Pat. No. 5,763,447). Further therapeutic uses include treatment of sinusitis (PCT International Publication WO 98/03177), otitis media (PCT International Publication WO 97/29756), dry eye, retinal detachment, nasolacrimal duct obstruction, the treatment of female infertility and irritation due to vaginal dryness via increased mucus secretions and hydration of the epithelial surface, and enhancing the performance of athletes.

The compounds of Formula I may be administered orally, topically, parenterally, by inhalation or spray, intra-operatively, rectally, or vaginally in dosage unit formulations containing conventional non-toxic pharmaceutically acceptable carriers, adjuvants and vehicles. The term topically as used herein includes patches, gels, creams, ointments, suppositories, pessaries, or nose, ear or eye drops. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers or diluents or adjuvants and, if desired, other active ingredients. One such carrier would be sugars, where the compounds may be intimately incorporated in the matrix through glassification or simply admixed with the carrier (e.g., lactose, sucrose, trehalose, mannitol) or other acceptable excipients for lung or airway delivery.

One or more compounds of general Formula I may be administered separately or together, or separately or together with: mucolytics such as DNAse (Pulmozyme®) or acetylcysteine, antibiotics, including but not limited to inhaled Tobramycin®; non-steroidal anti-inflammatories, antivirals, vaccines, decongestants and corticosteroids.

The pharmaceutical compositions containing compounds of general Formula I may be in a form suitable for oral use, for example, as tablets, caplets, lozenges, aqueous or oily suspensions, dispersible powders or granules, emulsion, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents; for example, corn starch, or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example, peanut oil, liquid paraffin or olive oil.

Aqueous suspensions contain the active materials in admixture with excipients suitable for the manufacture of aqueous suspensions. Such excipients are suspending agents, for example: sodium carboxymethylcellulose, methylcellulose and sodium alginate. Dispersing or wetting agents may be a naturally-occurring phosphatide or condensation products of an allylene oxide with fatty acids, or condensation products of ethylene oxide with long chain aliphatic alcohols, or condensation products of ethylene oxide with partial esters from fatty acids and a hexitol, or condensation products of ethylene oxide with partial esters derived from fatty acids and hexitol anhydrides. Those skilled in the art will recognize the many specific excipients and wetting agents encompassed by the general description above. The aqueous suspensions may also contain one or more preservatives, for example, ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredients in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents, may also be present.

Compounds of Formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle. The sterile injectable preparation may be a sterile injectable solution or suspension in a non-toxic parentally acceptable diluent or solvent. Among the acceptable vehicles and solvents that may be employed are sterile water, saline solution, or Ringer's solution. The compounds of general Formula I may also be administered in the form of suppositories for ear, rectal or vaginal administration of the drug. These compositions can be prepared by mixing the drug with a suitable non-irritating excipient which is solid at ordinary temperatures but liquid at the body temperature and will therefore melt to release the drug. Such materials are cocoa butter and polyethylene glycols.

Solutions of compounds of Formula I may be administered by intra-operative installation at any site in the body.

Single dosage levels of the order of from about 1 to about 400 mg, preferably in the range of 10 to 300 mg, and most preferably in the range of 25 to 250 mg, are useful in the treatment of the above-indicated respiratory conditions. Single dosage levels of the order of from about 0.0005 to about 5 mg, preferably in the range of 0.001 to 3 mg and most preferably in the range of 0.025 to 1 mg, are useful in the treatment of the above-indicated ophthalmic conditions. The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

The synthetic methods described below encompass several synthetic strategies for producing $P^1,P^4$-di(uridine 5')-tetraphosphate. Generally, all the methods use uridine or uridine nucleotide compounds from Formula IIa–d as starting materials, which are dissolved in a polar, aprotic organic solvent (e.g. dimethylformamide, dimethylsulfoxide, dioxane, N-methylpyrrolidone, trimethylphosphate) and a hydrophobic amine (e.g. triethylamine, tributylamine, trioctylamine, 2,4,6-collidine, tetrabutylammonium, tri- and tetraalkyl amines, heterocyclic amines). The product is obtained by phosphorylating with a phosphorylating agent from Formula IV (e.g. phosphorus oxychloride, pyrophosphate, pyrophosphorylchloride) or activating a phosphate group with an activating agent from Formula III (e.g. carbonyldiimidazole, an alkyl or aryl carbodiimide, an alkyl or aryl phosphochloridate), respectively, with subsequent purification various means well known to those of skill in the art, including, but not limited to, ion chromatography (e.g. DEAE Sep hadex, DEAE cellulose, Dowex 50, anion and cation exchange resins).

The pyrimidine β-D-ribofuranosyl starting materials uridine, uridine 5'-monophosphate (UMP), uridine 5'-diphosphate (UDP), and uridine 5'-triphosphate (UTP) are shown as free acids in Formulas IIa–d below, respectively. These materials are all commercially available in large quantity in various salt forms.

Formula IIa:

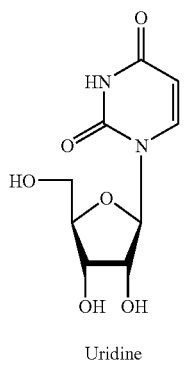

Uridine

Formula IIb:

and salts thereof;

UMP

Formula IIc:

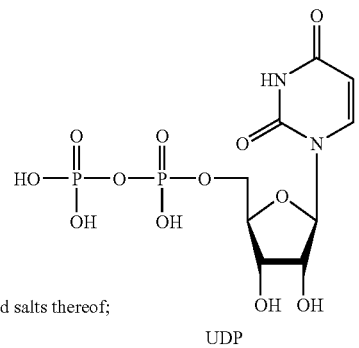

and salts thereof;

UDP

Formula IId:

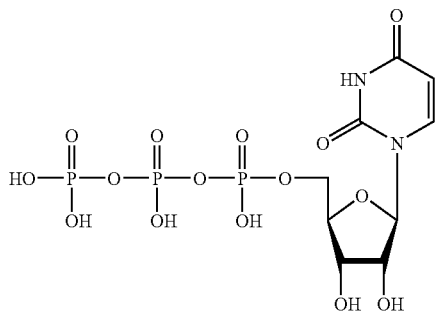

UTP and salts thereof.

The activating agents carbodiimide, activated carbonyl, and activated phosphorus compounds are shown in the general Formulas IIIa–c below, respectively.

Formula IIIa:

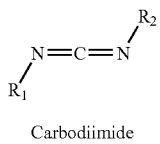

Carbodiimide wherein $R_1$ and $R_2$ are $C_1$–$C_8$ alkyl or cycloalkyl, $C_1$–$C_8$ optionally substituted alkyl or cycloalkyl (e.g. hydroxy and amino groups); aryl or optionally substituted aryl (e.g. hydroxy and amino groups). Preferred compounds of Formula IIIa are dicyclohexylcarbodiimide and 1-(3-Dimethylaminopropyl)-3-ethylcarbodiimide hydrochloride.

Formula IIIb:

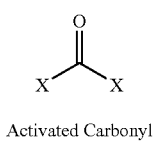

Activated Carbonyl wherein X is N-imidazolyl, N-tetrazolyl, and or halogen. Preferred compounds of Formula IIIb are carbonyldiimidazole and carbonylditriazole.

Formula IIIc:

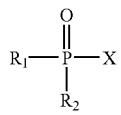

Activated Phosphorus wherein $R_1$ and $R_2$ are $C_1$–$C_8$ alkyl or cycloalkyl, $C_1$–$C_8$ optionally substituted alkyl, alkoxy or cycloalkyl (e.g. hydroxy and amino groups); aryl, alkoxy or optionally substituted aryl or alkoxy (e.g. hydroxy and amino groups) and/or halogen; and X is halogen. Preferred compounds of Formula IIIc are diphenylphosphorochloridate, phenyl phosphorodichloridate, phenylphosphonic dichloride and diphenylphosphinic chloride.

The mono- and diphosphorylating agents are shown below in general Formulas IVa–b.

Formula IVa:

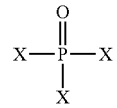

Monophosphorylating Agents wherein X is halogen. Preferred compound of Formula IVa is phosphorus oxychloride.

Formula IVb:

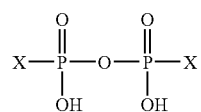

Diphosphorylating Agents wherein X is oxygen, hydroxy, or halogen, and salts thereof. Preferred compounds of Formula IVb are pyrophosphoryl chloride and pyrophosphate.

Those having skill in the art will recognize that the present invention is not limited to the following examples and that the steps in the following examples may be varied.

EXAMPLE 1

Method for the Production of Diuridine Tetraphosphate, Tetrasodium Salt Using Uridine 5'-Diphosphate Uridine 5'-diphosphate disodium salt (Yamasa, Choshi, Japan; 600 grams) was dissolved in deionized water (5.4 L). The solution was passed through a Dowex 50W×4 H⁺ (Dow Chemical) column. The fractions containing uridine 5'-diphosphate were pooled and neutralized with tributylamine (Aldrich, St. Louis; 300 mL). The neutralized fractions were concentrated to an oil by using a rotary evaporator at a bath temperature of 55–60° C. The oil was dissolved in dry dimethylformamide (Aldrich, 3 L) and then dried by concentrating to an oil using a rotary evaporator (55–60° C. bath temperature). This step was repeated twice. The oil was again dissolved in dimethylformamide (3 L) and 1,1-carbonyldiimidazole (Aldrich; 100 g) was added. The solution was heated at 50° C. for 2½ hours. An additional amount of activating agent (33 grams) was added and heating continued for a further 2½ hours. The solution was again concentrated to an oil on a rotary evaporator (bath temperature at 55–60° C). The resulting oil was dissolved in deionized water to a conductivity equal to that of 0.2 M $NH_4HCO_3$. The solution was then loaded into a column of Sephadex DEAE-A25 (Pharmacia, Upsala, Sweden; pre-swollen in 1.0 M $NaHCO_3$ and washed with 2 column volumes of deionized $H_2O$). The column was eluted with the following solutions in the following order: 60 L of 0.25 M $NH_4HCO_3$, 120 L of 0.275M $NH_4HCO_3$, 40 L of 0.30 M $NH_4HCO_3$ and 40 L of 0.35 M $NH_4HCO_3$. The fractions having sufficient amounts of pure diuridine tetraphosphate were pooled as determined by HPLC analysis and concentrated on a rotary evaporator (bath temperature at 55–60° C.). The resulting residue was dissolved in deionized water (1.5 L) and concentrated on a rotary evaporator. This step was repeated 15 times or until excess of bicarbonate buffer was removed. The resulting oil was dissolved in a sufficient amount of deionized water to form a ca. 10% solution, the solution charged to a Dowex 50W×4 $Na^+$ (Dow) column and eluted with deionized water. The fractions containing $U_2P_4$ were pooled and concentrated to a ca. 10–15% solution, which was lyophilized to yield $U_2P_4$ tetrasodium salt as a white solid (150 g approximately 25% yield based on uridine 5'-diphosphate).

Structure Elucidation of $P^1,P^4$-di(uridine 5')-Tetraphosphate, Tetrasodium Salt Due to the lack of adequate spectroscopic data of non-adenylated dinucleotides in the literature, a full structure elucidation of $P^1,P^4$-di(uridine 5')-tetraphosphate, tetrasodium salt was performed by employing modern analytical techniques. The molecular weight was determined by mass spectrometry to be 878 [m/z 855, $(M-Na^+)^-$], confirming the molecular formula $C_{18}H_{22}N_4O_{23}P_4 \cdot 4Na$. The exact mass measured for $C_{18}H_{22}N_4O_{23}P_4 \cdot 3Na$ [$(M-Na^+)^-$: calculated 854.9318] was 854.9268. The measured mass differed from the theoretical mass by 5.0 millimass units (5.9 ppm) for a confidence level of 99.7%. Karl Fisher moisture analysis gave a value of 1.73% $H_2O$ and further confirmation of the molecular formula was obtained from elemental analysis: calculated for Na=10.70, found 10.81%; C:P ratio calculated 1.74, found 1.80, based on the molecular formula: $C_{18}H_{22}N_4O_{23}P_4 \cdot 4.2Na \cdot 1.1H_2O$ (FW=902.4 g/mol). The infrared spectrum showed a broad signal at 3422 $cm^{-1}$ and a signal at 1702 $cm^{-1}$, indicating the presence of hydroxyl (O—H stretch) and carbonyl (C=O stretch) functional groups. In addition, a phosphate P=O stretch was observed at 1265 $cm^{-1}$. The UV spectrum in water displayed a $\lambda_{max}$ of 262 nm with a molar absorptivity ($\epsilon$) of 17,004. The specific rotation at 25° C. (c=1, $H_2O$) was determined by polarimetry to be −9.56°.

The NMR spectra are: $^1H$ NMR ($D_2O$, TMS) δ 4.11 (m, 2H), 4.14 (m, 1H), 4.25 (m, 1H), 4.27 (m, 1H), 5.84 (d, J=8.1 Hz, 1H), 5.86 (d, J=5.4 Hz, 1H), 7.81 (d, J=8.1 Hz); $^{13}C$ NMR ($D_2O$, TMS) δ 65.1 (d, J=5.5 Hz), 69.7, 73.5, 83.4 (d, J=9.4 Hz), 88.1, 102.8, 141.5, 152.9, 167.5; $^{31}P$ NMR ($D_2O$, $H_3PO_4$ std) δ −22,32 (m),−10.75 (m). The $^1H$ coupled $^{31}P$ spectrum showed a broadening of the multiplet at δ −10.75 ppm due to the introduction of $^1H$ coupling. This multiplet was therefore confirmed as $P_\alpha$. There was no effect of $^1H$ coupling on the multiplet at −22.23 ppm, assigning this by default as Pβ. A Nuclear Overhauser Effect (NOE) was observed for $H_6$ to the $H_{2'}$ and $H_{3'}$ sugar protons. Because it is not possible for $H_5$ to show an NOE to the sugar protons, $H_6$ is confirmed. Additionally, $N_1$ substitution is confirmed, because no pyrimidine-sugar NOE is possible for an $N_3$ substituted structure.

Additional 2-dimensional NMR experiments were conducted to verify connectivity. HMQC shows connectivity for $H_5$ to $C_5$ and $H_6$ to $C_6$, confirming $C_5$ and $C_6$. COSY and NOE connectivity were observed for $H_5$ to $H_6$, verifying $H_5$. HMBC 3-bond connectivity was observed for: $H_6$ to $C_{1'}$, $C_6$ to $H_{1'}$, $H_{1'}$ to $C_2$, $H_6$ to $C_2$. These data thus confirm $H_1$, $C_2$ and $N_1$ substitution. COSY connectivity of $H_{1'}$ to $H_{2'}$ confirms $H_{2'}$ and HMQC connectivity of $H_{1'}$ to $C_{1'}$ and $H_{2'}$ to $C_{2'}$ confirms $C_{1'}$ and $C_{2'}$. Additionally, HMBC shows 2-bond J connectivity from $H_5$ to $C_4$, confirming $C_4$. A $^{13}C$ DEPT spectrum with mult=1.5 shows the carbon at 65.1 inverted relative to all other carbons. This observation confirms that $C_{5'}$ is a methylene. The coupling of $^{31}P$ to carbons at 65.1 and 83.4 confirms $C_{5'}$ and $C_{4'}$, because $C_{4'}$ is the only coupled methyne. In addition, HMQC shows connectivity for $C_{5'}$ to $H_{5'}$ and $C_{4'}$ to $H_{4'}$, confirming $H_{4'}$ and $H_{5'}$. An NOE was observed for $H_{1'\ to\ H4'}$, $H_6$ to $H_{2'}$ and $H_6$ to $H_{3'}$, confirming the β anomer sugar configuration.

In conclusion, $P^1,P^4$-di(uridine 5')-tetraphosphate, tetrasodium salt was synthesized on a 150 g scale in 25% yield from commercially available starting materials with a total reaction time of 5 hours. The crude product was efficiently purified by ion exchange chromatography and the structure of the reaction product was unambiguously proven using mass spectroscopic, NMR and other analytical techniques.

EXAMPLE 2

Method for the Production of Diuridine Tetraphosphate Tetraammonium Salt Using Uridine 5'-Monophosphate Uridine 5'-monophosphate (Sigma, Milwaukee, 3.0 g, 9.26 mmol) was dissolved in dry DMF (10 mL) and tributylamine (Aldrich, 2 mL). The solution was evaporated in vacuo at 40° C. to an oil. The residue was dissolved in dry DMF (Aldrich, 8 mL) to form a solution. Carbonyldiimidazole (Aldrich, 1.65 g, 10.18 mmol) was added to this solution. The reaction was heated at 50° C. for one hour. Uridine 5'-triphosphate (Yamasa, 5.60 g, 10.18 mmol) prepared as the anhydrous tributylammonium salt in DMF (5 mL) and tributylamine (2 mL), as described in Example 3 below, was added to the reaction solution. The mixture was allowed to stir at 50° C. for three days when the solution was evaporated in vacuo to an oil, redissolved in water (5 mL) and purified by column (300×50 mm) chromatography (Sephadex DEAE-A25, 40–120μ, Aldrich, pre-swollen in 1.0 M $NaHCO_3$ and washed with 2 column volumes of deionized $H_2O$ ($H_2O$→0.30 M $NH_4HCO_3$ gradient). The pure fractions were concentrated in vacuo at 35° C., and $H_2O$ added and reevaporated 5 times to obtain diuridine tetraphosphate tetrammonium salt as a white solid (2.37 g, 30% yield): 92.11% pure by HPLC with the same retention time as the standard. In addition, the tetrammonium salt was analyzed by FABMS to give a mass of $[C_{18}H_{25}N_4O_{23}P_4$ $(M-H^+)^-$: calculated 788.9860] 788.9857, confirming a parent formula of $C_{18}H_{26}N_4O_{23}P_4$ for the free acid].

EXAMPLE 3A

Method for the Production of Diuridine Tetraphosphate Using Uridine 5'-Triphosphate (UTP)

A solution of uridine 5'-triphosphate (UTP) trisodium salt (ProBioSint, Varese, Italy; 5.86 g, 0.01 mol) in water (5 mL)

was passed through a column of BioRad AG-MP 50 (Aldrich) strong cation exchange resin in its tributylamine form (50 mL bed volume) and eluted with distilled water (about 300 mL). To this solution was added tributylamine (Aldrich; 5 mL), and the suspension shaken until the pH of the aqueous fraction had risen to 8. The layers were separated and the aqueous solution evaporated to small volume, then lyophilized overnight. The residue was dissolved in dry dimethylformamide (Aldrich; 20 mL) and the solvent evaporated at 0.1 mmHg. The dried tributylamine salt was made up to 100 mL with anhydrous acetone to yield a stock solution (0.1 M in UTP). Dicyclohexylcarbodiimide (DCC) (Baker, Phillipsburg; 0.227 g, 1.2 mmol) was added to an aliquot of the foregoing UTP solution (10 mL, 1.0 mmol) and the solution stirred at room temperature for 30 minutes. The mixture was added to the triethylamine salt of uridine 5'-monophosphate (2.0 mmol, prepared by addition of triethylamine (0.5 mL) to a solution of uridine 5'-monophosphate (UMP) (Sigma; 0.648 g in DMF), and evaporating to dryness). This suspension was then evaporated to dryness, the residue made up to 5.0 mL in dry DMF, and set aside at 40° C. for 24 hours. The reaction mixture was separated by semipreparative ion-exchange chromatography (Hamilton PRP X-100 column), eluting with a gradient of 0–1.0 M ammonium bicarbonate, 5 mL/min, 30 minutes. The dinucleotide tetraphosphate eluted between 21 and 23 minutes; the product (76.7% yield based on UTP) was quantitated by comparison of its ultraviolet absorption at $\lambda_{max}$ 263 nm with that of a standard solution of $P^1,P^4$-di(uridine 5')-tetraphosphate.

EXAMPLE 3B

Method for the Production of Diuridine Tetraphosphate Using Uridine 5'-Triphosphate (UTP) and an Excess of Activating Agent Conversion of UTP to $P^1,P^4$-di(uridine 5')-tetraphosphate can be enhanced by activation of the tributylamine salt (0.1 mmol) with a large excess of DCC (0.1g, 0.5 mmol); in this case the deposited dicyclohexylurea was removed by filtration, the reaction mixture extracted with ether (10 mL) and the residue dissolved in dry DMF prior to treatment with tributylamine UMP (0.2 mmol). Upon chromatographic separation of the reaction mixture and quantitation by ultraviolet absorption as in Example 3A above, the uridine tetraphosphate product constituted 50.7% of the uridylate species in the mixture, corresponding to a conversion from UTP of 95.9%.

EXAMPLE 4A

Method for the Production of Diuridine Tetraphosphate Using Uridine 5'-Monophosphate Activated with Carbonyldiimidazole Uridine 5'-monophosphate (UMP) (0.324 g, 1.0 mmol) was dissolved in a mixture of dry DMF (5 mL) and tributylamine (237 µL, 1 mmol) the solution was evaporated to dryness, then twice more with DMF to yield the anhydrous tributylamine salt. The residue was dissolved in DMF (5 mL) and carbonyldiimidazole (CDI) (0.81 g, 5 mmol) added. The solution was set aside for 3 hours, then methanol 324 µL, 8 mmol) added to destroy the excess of CDI. The solution was set aside for one hour. Tributylamine pyrophosphate (Sigma, 0.228 g, 0.5 mmol) was added and the suspension stirred under nitrogen at room temperature. After 3 hours the reaction was quenched with water and the mixture subjected to HPLC as in Example 3A above. Yield of $P^1,P^4$-di(uridine 5')-tetraphosphate as quantitated by its absorbance at 263 nm was 9.3%.

EXAMPLE 4B

Method for the Production of Diuridine Tetraphosphate Using Uridine 5'-Monophosphate Activated with Diphenyl Phosphochloridate The anhydrous tributylamine salt of UMP (1.0 mmol), prepared essentially as above, was dissolved in a mixture of dry dioxane (5 mL) and DMF (1 mL). Diphenyl phosphochloridate (0.3 mL) and tributylamine (0.3 mL) were added and the solution set aside at room temperature for 3 hours. The solvent was evaporated and the residue shaken with ether (10 mL), then set aside at 4° C. for 30 minutes. The ether was decanted and the residue was dissolved in a solution of tributylamine pyrophosphate (0.228 g, 0.5 mmol) in DMF (3 mL). The solution was stored under nitrogen at room temperature. After 3 hours the reaction was quenched with water and the mixture subjected to HPLC as in Example 3A above. Yield of $P^1,P^4$-di(uridine 5')-tetraphosphate as quantified by its absorbance at 263 nm was 9.6%.

EXAMPLE 5

Method for the Production of Diuridine Tetraphosphate Using Uridine, Phosphorus Oxychloride and Pyrophosphate Uridine (Aldrich, 0.244 g, 1 mmol) was dissolved in trimethyl phosphate (Aldrich, 5 mL) and tributylamine (466 uL, 2 mmol) added. The solution was stirred at 0 degrees during the addition of phosphorus oxychloride (0.153 g (93.2 uL), 1 mmol), and the resulting suspension stirred at 0° C. for 3 hours. Tributylamine pyrophosphate (0.228 g) was added and the suspension stirred at room temperature for 3 hours. The reaction was quenched with 1.0 M aqueous triethylamine bicarbonate and the mixture extracted with methylene chloride to remove trimethyl phosphate. The aqueous solution was subjected to HPLC as in Example 3A above. Conversion of uridine to $P^1,P^4$-di(uridine 5')-tetraphosphate as quantitated by absorbance of the latter at 263 nm was 6.83%.

EXAMPLE 6

Method for the Production of Diuridine Tetraphosphate Using Uridine 5'-Monophosphate and Pyrophosphoryl Chloride Uridine 5'-monophosphate (UMP) (64.8 mg, 0.2 mmol) was dissolved in dry pyridine (1 mL) and stirred in ice during the addition of pyrophosphoryl chloride (13.9 uL (25 mg), 0.1 mmol). The solution became cloudy almost immediately, then a copious semicrystalline white precipitate formed which became a gummy mass within 1–2 minutes. The mixture was stored at room temperature overnight, then quenched with water and subjected to HPLC as in Example 3A above. Yield of $P^1,P^4$-di(uridine 5')-tetraphosphate as quantitated by its absorbance at 263 nm was 15.8%. A substantial amount of $P^1,P^3$-di(uridine 5'-triphosphate) (25.4%) was obtained as the major by-product.

EXAMPLE 7

Aqueous Stability and Solubility of $P^1,P^4$-di(uridine 5')-tetraphosphate, Tetrasodium Salt The solubility of $P^1,P^4$-di(uridine 5')-tetraphosphate, tetrasodium salt in water was determined by adding portions of solid to a known volume of deionized water until the solution became turbid. The maximum solubility in water was thus determined to be ca. 900 mg/mL. Stability studies of the solid or aqueous solutions incubated at low (5° C.) and elevated temperatures (40° C.) showed that less than 1.5% degradation occurs over a three month period as determined by HPLC analysis. The tetrasodium salt of $P^1,P^4$-di(uridine 5')-tetraphosphate was thus determined to have an excellent solubility and stability profile suitable for pharmaceutical applications.

EXAMPLE 8

Toxicity of $P^1,P^4$-di(uridine 5')-tetraphosphate, Tetrasodium Salt in Animals The nonclinical toxicologic profile of $P^1,P^4$-di(uridine 5')-tetraphosphate, tetrasodium salt has been evaluated in a battery of genetic toxicology assays that include the bacterial reverse mutation assay, the in vitro mammalian cytogenetic test, the in vitro mammalian cell gene mutation test, and the micronucleus cytogenetic assay in mice. A study in rabbits examined local ocular tolerance and subchronic ocular toxicity after multiple daily administrations over a six-week period. In addition, $P^1,P^4$-di(uridine 5')-tetraphosphate, tetrasodium salt has also been tested in two single-dose acute inhalation toxicity studies in rat and dog, and one single-dose acute intravenous toxicity study in dogs.

The results of these studies show that $P^1,P^4$-di(uridine 5')-tetraphosphate, tetrasodium salt is nongenotoxic in a battery of genetic toxicology assays. No adverse findings were seen in the ocular toxicology studies. A low degree of acute toxicity was seen in single dose inhalation (rats, dogs) and intravenous (dogs) toxicity studies. $P^1,P^4$-di(uridine 5')-tetraphosphate, tetrasodium salt was therefore determined to have an excellent toxicology profile with a wide safety margin for dosing in humans.

EXAMPLE 9

Safety and Efficacy of $P^1,P^4$-di(uridine 5')-tetraphosphate, Tetrasodium Salt in Normal Human Volunteers $P^1,P^4$-di(uridine 5')-tetraphosphate, tetrasodium salt was evaluated in a Phase I, double-blind, placebo-controlled, escalating dose, safety and tolerability study in 75 normal healthy male volunteers. Forty non-smokers and 35 smokers were evaluated in 5 dosing cohorts of 16 volunteers, comprised of 12 receiving a single aerosolized dose of $P^1,P^4$-di (uridine 5')-tetraphosphate, tetrasodium salt (20–400 mg) and 4 receiving placebo (normal saline). No serious adverse events were reported. There were no significant changes in $FEV_1$, FVC, MMEF, clinical laboratory, 12-lead ECG, or urinalysis results in either the placebo or active drug groups. In smokers, $P^1,P^4$-di(uridine 5')-tetraphosphate, tetrasodium salt produced a 2-fold to 7-fold dose-dependent increase in the weight of sputum expectorated within 5 minutes of dosing, and stimulation of sputum expectoration was sustained over the next hour of sputum collection. The effect of $P^1,P^4$-di(uridine 5')-tetraphosphate, tetrasodium salt to induce the expectoration of sputum in non-smokers was also observed. In conclusion, $P^1,P^4$-di(uridine 5')-tetraphosphate, tetrasodium salt is safe and well-tolerated in normal male subjects and is effective in stimulating the expectoration of sputum when compared to placebo.

What is claimed is:

1. A process for the synthesis of a compound of Formula I, and pharmaceutically acceptable salts thereof, said process comprising:

a) dissolving a first uridine nucleotide compound of one of the Formulas IIb–d in a polar, aprotic organic solvent and a hydrophobic amine;

b) activating a phosphate group of said first uridine nucleotide compound with an activation agent of one of the Formulas IIIa–b and reacting with a second uridine nucleotide compound of Formulas IIb–d to yield a compound of Formula I; and c) purifying by chromatography said compound of Formula I, or a pharmaceutically acceptable salt thereof;

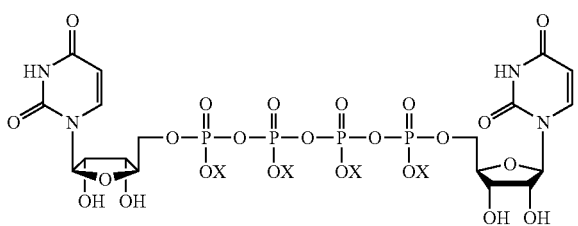

Formula I wherein:

X is selected from the group consisting of: $Na^+$, $NH_4^+$ and H, provided that all X groups are not H;

Formula IIb:

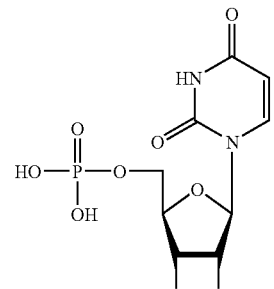

and salts thereof;

UMP

Formula IIc:

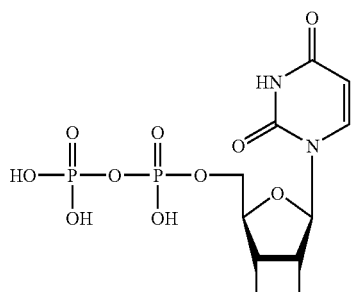

and salts thereof;

UDP

Formula IId:

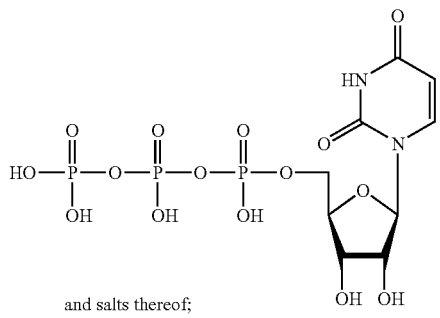

and salts thereof;

Formula IIIa:

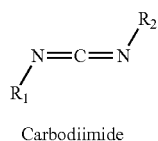

Carbodiimide wherein $R_1$ and $R_2$ are independently selected from the group consisting of: $C_1$–$C_8$ alkyl, $C_1$–$C_8$ cycloalkyl, and aryl, wherein said alkyl is optionally substituted with N,N-dimethylamino groups;

Formula IIIb:

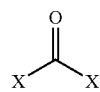

Activated Carbonyl wherein X is independently selected from the group consisting of: N-imidazolyl, N-tetrazolyl and halogen;
wherein the polar, aprotic organic solvent comprises N,N-dimethylformamide or dioxane.

2. The process of claim 1, wherein said hydrophobic amine is a trialkyl amine.

3. The process of claim 2, wherein said trialkyl amine is triethyl amine, tributyl amine or trioctyl amine.

4. The process of claim 3, wherein said first uridine nucleotide compound of step a) is uridine triphosphate or a trialkyl ammonium salt thereof.

5. The process of claim 1, wherein said first uridine nucleotide compound of step a) is uridine triphosphate or a trialkyl ammonium salt thereof.

6. The process of claim 5, wherein said second uridine nucleotide compound is uridine monophosphate or a trialkyl ammonium salt thereof.

7. The process of claim 5, wherein said second uridine nucleotide compound is a tributyl ammonium salt of uridine monophosphate.

8. The process of claim 5 wherein said activating agent in step b) is a carbodiimide of Formula IIIa.

9. The process of claim 8, wherein said carbodiimide is dicyclohexyl carbodiimide or b 1-(3-dimethylaminopropyl)-3-ethylcarbodiimide hydrochloride.

10. The process of claim 1, wherein said activating agent in step b) is a carbodiimide of Formula IIIa.

11. The process of claim 10, wherein said carbodiimide is dicyclohexyl carbodiimide or 1-(3-dimethylaminopropyl)-3-ethylcarbodiimide hydrochloride.

12. A process for the synthesis of a compound of Formula I, and pharmaceutically acceptable salts thereof, said process comprising:
   a) dissolving a first uridine nucleotide compound of one of the Formulas IIb–d in a polar, aprotic organic solvent and a hydrophobic amine;
   b) activating a phosphate group of said first uridine nucleotide compound with an activation agent of one of the Formulas IIa–b and reacting with a second uridine nucleotide compound of Formulas IIb–d to yield a compound of Formula I; and
   c) purifying by chromatography said compound of Formula I, or a pharmaceutically acceptable salt thereof;

Formula I

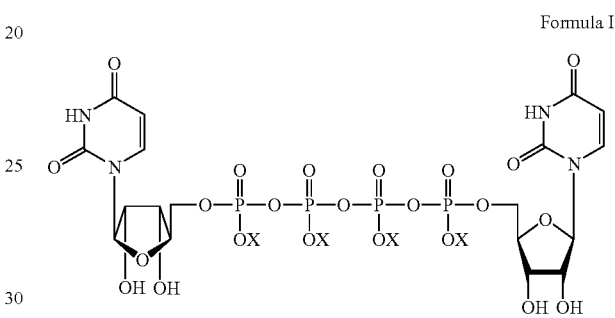

X is selected from the group consisting of: Na$^+$, NH$_4^+$ and H, provided that all X groups are not H;

Formula IIb:

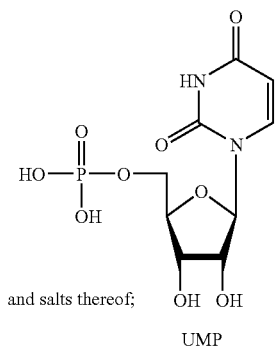

and salts thereof;

UMP

Formula IIc:

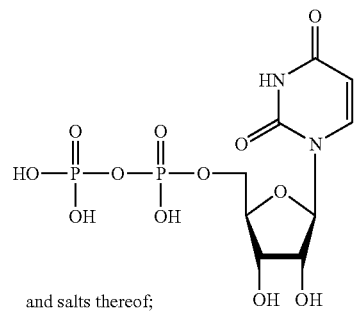

and salts thereof;

UDP

-continued

Formula IId:

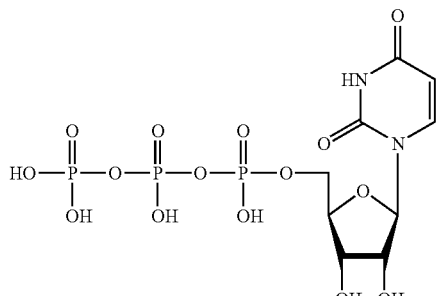

and salts thereof;

UTP

Formula IIIa:

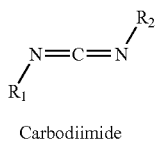

Carbodiimide wherein R₁ and R₂ are independently selected from the group consisting of: $C_1$–$C_8$ alkyl, $C_1$–$C_8$ cycloalkyl, and aryl, wherein said alkyl is optionally substituted with N,N-dimethylamino groups;

Formula IIIb:

Activated Carbonyl wherein X is independently selected from the group consisting of: N-imidazolyl, N-tetrazolyl and halogen;

wherein the polar, aprotic organic solvent comprises dimethylsulfoxide, N-methylpyrrolidone, or trimethylphosphate.

13. The process of claim 12, wherein said hydrophobic amine is a trialkyl amine.

14. The process of claim 13, wherein said trialkyl amine is triethyl amine, tributyl amine or trioctyl amine.

15. The process of claim 14, wherein said first uridine nucleotide compound of step a) is uridine triphosphate or a trialkyl ammonium salt thereof.

16. The process of claim 12, wherein said first uridine nucleotide compound of step a) is uridine triphosphate or a trialkyl ammonium salt thereof.

17. The process of claim 16, wherein said second uridine nucleotide compound is uridine monophosphate or a trialkyl ammonium salt thereof.

18. The process of claim 17, wherein said second uridine nucleotide compound is a tributyl ammonium salt of uridine monophosphate.

* * * * *